(12) United States Patent
Platzek et al.

(10) Patent No.: US 6,978,662 B2
(45) Date of Patent: Dec. 27, 2005

(54) RHEOMETER

(75) Inventors: Wolfgang Platzek, Karlsruhe (DE); Pierre Reinheimer, Strasbourg (FR)

(73) Assignee: Thermo Electron (Karlsruhe) GmbH, Karlsruhe (DE)

( * ) Notice: Subject to any disclaimer, the term of this patent is extended or adjusted under 35 U.S.C. 154(b) by 0 days.

(21) Appl. No.: 10/726,579

(22) Filed: Dec. 4, 2003

(65) Prior Publication Data

US 2004/0118188 A1     Jun. 24, 2004

(30) Foreign Application Priority Data

Dec. 21, 2002 (DE) .............................. 102 60 981

(51) Int. Cl.$^7$ ............................................. G01N 11/14
(52) U.S. Cl. ................... 73/54.42; 73/54.01; 73/54.23; 73/54.28; 73/54.31; 73/54.39
(58) Field of Search .................... 73/54.01, 54.02, 73/54.23, 54.28, 54.29, 54.31, 54.39, 54.42

(56) References Cited

U.S. PATENT DOCUMENTS

| | | | | |
|---|---|---|---|---|
| 3,182,494 A | * | 5/1965 | Beatty et al. ................. | 374/48 |
| 3,769,830 A | * | 11/1973 | Porter et al. .................. | 374/48 |
| 3,818,751 A | * | 6/1974 | Karper et al. ................. | 374/46 |
| 4,643,021 A | * | 2/1987 | Mattout ...................... | 73/54.28 |
| 4,794,788 A | * | 1/1989 | Masters et al. ............. | 73/54.27 |
| 4,884,437 A | * | 12/1989 | Constant et al. ........... | 73/54.01 |
| 5,253,513 A | * | 10/1993 | Van Arsdale et al. ...... | 73/54.41 |
| 5,520,042 A | | 5/1996 | Garritano | |
| 5,905,196 A | * | 5/1999 | Parshall ..................... | 73/54.31 |
| 6,240,770 B1 | * | 6/2001 | Raffer ....................... | 73/54.28 |
| 6,571,610 B1 | * | 6/2003 | Raffer ....................... | 73/54.35 |
| 2002/0178796 A1 | * | 12/2002 | Barbe et al. ............... | 73/54.39 |
| 2004/0173009 A1 | * | 9/2004 | Doe et al. .................. | 73/54.02 |
| 2004/0226349 A1 | * | 11/2004 | Feustel ...................... | 73/54.02 |

FOREIGN PATENT DOCUMENTS

| | | | |
|---|---|---|---|
| DE | 23 26 256 | 12/1973 | |
| DE | 37 31 317 | 3/1988 | |
| DE | 100 58 399 | 5/2001 | |
| EP | 0 039 790 | 11/1981 | |
| GB | 2195777 A | * 4/1988 | .......... G01N 11/14 |
| GB | 2356937 A | * 6/2001 | .......... G01N 11/14 |

OTHER PUBLICATIONS

"Melcor Thermoelectric Plate Chillers/Heaters", available on the Internet at <http://www.labsafety.com/store>.*
"AR 2000 Accessories", available on the Internet at <http://www.tainst.com/products/ar2000accessories.html>.*
"Center-Hole and Round Modules", available on the Internet at <http://www.tetech.com/modules/center-hole.shtml>.*

* cited by examiner

*Primary Examiner*—John E. Chapman
*Assistant Examiner*—David A. Rogers
(74) *Attorney, Agent, or Firm*—Paul Vincent

(57) ABSTRACT

A rheometer has an upper measuring part and a lower measuring part, between which a measuring chamber is formed for receiving a sample of a substance to be examined, wherein the two measuring parts can be moved relative to each other and, in particular, can be rotated or pivoted. Moreover, a heating device is provided for heating at least the lower measuring part and therefore the sample. The lower measuring part comprises a support part carrying the sample which can be heated through application of an electrical voltage. The support part is preferably made from glass which is itself electrically conducting and/or which can be provided with an electrically conducting medium.

15 Claims, 1 Drawing Sheet

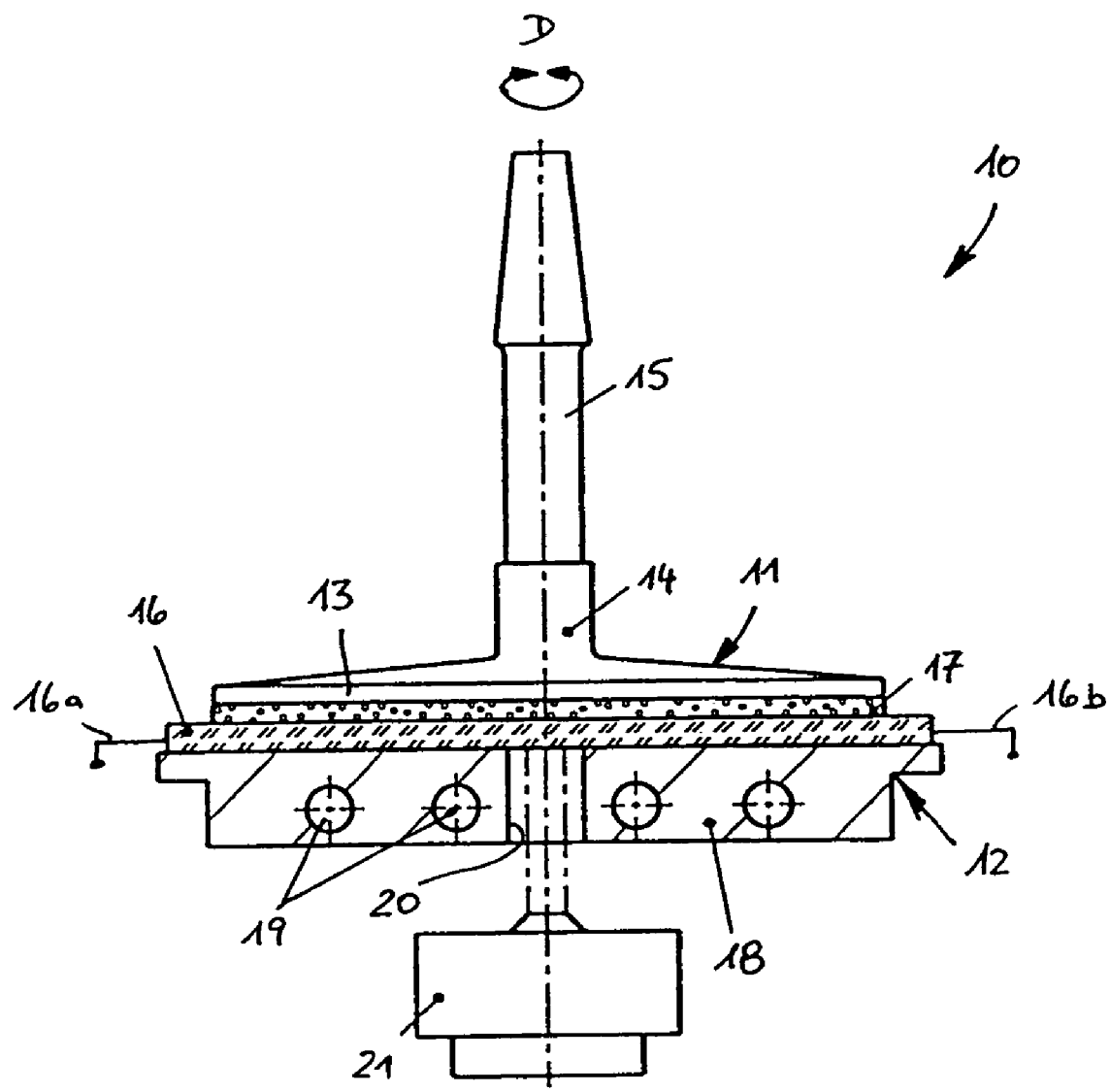

RHEOMETER

This application claims Paris Convention priority of DE 102 60 981.0 filed Dec. 21, 2002 the complete disclosure of which is hereby incorporated by reference.

BACKGROUND OF THE INVENTION

The invention concerns a rheometer comprising an upper measuring part and a lower measuring part, between which a measuring chamber is formed for receiving a sample of a substance to be examined, wherein the two measuring parts can be moved relative to each other and, in particular, be turned or pivoted, and with a heating device for heating at least the lower measuring part.

A rheometer for determining the characteristic rheological values of a viscous substance usually comprises a lower stationary measuring part (stator) and an upper measuring part (rotor) which can be axially adjusted, rotated, or pivoted and between which a measuring chamber is formed to receive a sample of the substance to be examined. The forces and tensions produced through relative motion between the upper and lower measuring parts are measured and can be used to calculate the desired characteristic rheological values. The characteristic rheological values depend i.a. on the temperature of the sample during the measurement. To obtain reproducible characteristic rheological values, one therefore tries to heat the sample to a predetermined temperature and keep it at this temperature throughout the entire measurement. To obtain exact measured data, it is thereby necessary that the temperature is homogeneously distributed within the sample of the substance to be examined. This is not the case in many heating devices of conventional structure.

In many cases, a heat exchanger in the form of a plate is used as a heating device which is penetrated by channels in which warm fluid flows. Since the channels in the plate have a mutual separation, the plate does not heat uniformly in all regions thereby making it more difficult to obtain homogeneous temperature distribution in the sample of the substance to be examined.

Moreover, it is sometimes desirable to observe the sample during measurement using a video camera for detecting and evaluating the particle distribution within the sample. Towards this end, a small gap is conventionally left in the plate of the heat exchanger and the sample is observed through this gap. The gap may disadvantageously prevent a homogeneous temperature distribution in the sample with the inhomogeneity, moreover, occurring exactly at the location of observation or measurement, thereby disadvantageously influencing the accuracy of the measured result.

It is the underlying purpose of the present invention to produce a rheometer of the above-mentioned type, with which the lower measuring part can be heated with a homogeneous temperature distribution.

SUMMARY OF THE INVENTION

This object is achieved in accordance with a rheometer comprising the features of the independent claim. The lower measuring part comprises a support part carrying the sample which can be heated through application of an electrical voltage. The support part may be directly heated and either consists of an electrically conducting, preferably non-metallic material and/or is provided with an electrically conducting medium, wherein the electrically conducting medium is embedded in the support part and/or may be rigidly disposed thereon in the form of a coating. Homogeneous temperature distribution on the measuring surface, i.e. the support surface of the support part where the sample of the substance to be examined is disposed, is obtained through electric heating of the support part due to its inherent resistance. The support part preferably consists of an electrically conducting glass and may be a plate, a cone, a cylindrical cup or have another geometrical shape. Other materials, in particular heat-resistant plastic material, ceramic material or semi-conductor materials can also be used. It has turned out, that when glass is used as a heating resistance, temperatures of more than 400° C. can be obtained. Moreover, temperature control produces high reaction sensitivity. In the following example, the support part is a glass plate.

At least a portion of the support part or the glass plate is preferably transparent. Due to the transparency of the support part or the glass plate, the sample can be observed during the measurement without having to provide a gap, i.e. a region of discontinuity, in the support part or plate. When the support part or glass plate is completely transparent, optical observation of the sample over the entire measuring surface is possible and not only in a predetermined narrow gap region.

Optical observation of the sample during the measurement preferably occurs through the support part or the glass plate. Towards this end, a camera, in particular a video camera, can be disposed below the support part or the glass plate or its transparent section in order to observe the sample. The camera may either be stationary or be movable relative to the support part or the glass plate and therefore relative to the sample. A lens of conventional construction may also be disposed between the camera and the sample.

After completion of a measurement, the support part or the glass plate may have to be cooled down to an initial temperature. This may be preferably effected by coupling the support part or the glass plate to a cooling device. The cooling device is preferably a heat exchanger in the form of a cooling plate which is penetrated by channels for a cooling medium. The support plate (glass plate) may be supported on the cooling device or cooling plate at the support plate side facing away from the sample. To also permit observation of the sample during the measurement in this case, at least one passage or gap should be formed in the cooling device or the cooling plate, through which the sample can be observed by the camera. A Peltier element may also be used as cooling device instead of a conventional heat exchanger.

Conventional rheometers have a separate temperature probe to determine the actual temperature which causes an additional inhomogeneity in the temperature distribution. In the inventive rheometer, the temperature of the sample of the substance to be examined can be determined via the inherent resistance of the support part or of the glass plate, which depends on the sample temperature and is, in particular, proportional thereto. Towards this end, a processing unit is preferably provided to determine the temperature of the sample in dependence on the resistance of the support part or glass plate.

The upper measuring part can also consist at least partially of glass and be directly heated as mentioned above. To increase the homogeneity of the temperature distribution, an upper, in particular, cap-like sample cover may additionally or alternatively be provided for the sample. The sample cover can consist of a non-metallic material of the mentioned type which can be directly heated as mentioned above. Further details with respect to the construction and heating of the support part can be extracted from the above description.

Further details and features of the invention can be extracted from the following description of an embodiment with reference to the drawing.

BRIEF DESCRIPTION OF THE DRAWING

FIG. 1 shows a section through the measuring structure of the rheometer in accordance with the invention.

DESCRIPTION OF THE PREFERRED EMBODIMENT

A rheometer 10 (shown only in sections in the figure) has an upper rotatable or pivotable measuring part (rotor) 11 which comprises a substantially horizontally oriented ceramic plate 13 which is mounted to the lower end of a vertical shaft 15 via a connecting piece 14, the shaft being pivotable or rotatable together with the connecting piece 14 and the plate 13 (indicated by double arrow D).

A sample 17 of a substance to be examined is disposed in a measuring chamber formed below the plate 13. The measuring chamber is delimited at its lower side by a support part in the form of a horizontal glass plate 16 whose upper support surface carrying the sample 17 extends substantially parallel to the lower side of the plate 13 to form a measuring space of constant height. The glass plate 16 is part of a stationary lower measuring part 12 (stator) and is supported with its lower side on a cooling plate 18 which is penetrated by channels 19 in which a cooling liquid may flow.

The glass plate 16 consists essentially of electrically conducting glass and is provided with connections 16a and 16b with which it can be connected to an electric voltage source (not shown). When an electric current flows through the glass plate 16 it is uniformly heated across its entire surface due to its inherent resistance and distributes this heat to the sample 17 lying on it which is thereby also uniformly heated.

A video camera 21 is disposed below a central opening 20 formed in the cooling plate 18. The video camera 21 is oriented to permit observation of the material sample 17 through the opening 20 in the cooling plate 18 and through the glass plate 16.

We claim:

1. A rheometer for examining a sample, the rheometer comprising:
   an upper measuring part;
   a lower measuring part, said upper and said lower measuring part defining a measuring chamber for receiving the sample, said lower measuring part having a support part which carries the sample and which is heated by directly applying an electrical voltage to said support part; and
   means for effecting relative motion between said upper and said lower measuring parts, wherein at least a portion of said support part is transparent.

2. The rheometer of claim 1, wherein said relative motion means effect a relative turning or pivoting between said upper and said lower measuring parts.

3. The rheometer of claim 1, further comprising a camera disposed below said transparent portion of said support part for observing the sample.

4. The rheometer of claim 1, wherein said support part is plate-shaped or cup-shaped.

5. The rheometer of claim 1, further comprising a processing unit for determining a temperature of the sample in dependence on a resistance of said support part.

6. The rheometer of claim 1, wherein said upper measuring part can be heated through application of an electrical voltage.

7. The rheometer of claim 1, wherein said support part consists essentially of an electrically conducting material.

8. The rheometer of claim 7, wherein said support part consists essentially of electrically conducting glass.

9. The rheometer of claim 1, wherein said support part comprises an integral electrically conducting medium.

10. The rheometer of claim 9, wherein said electrically conducting medium is embedded in or disposed on said support part.

11. The rheometer of claim 1, further comprising a hood-like cover which at least partially surrounds said upper measuring part and the sample, wherein said hood-like cover can be heated through application of an electrical voltage.

12. The rheometer of claim 11, wherein said hood-like cover consists essentially of glass which is electrically conducting or is provided with an electrically conducting medium.

13. The rheometer of claim 1, wherein said support part is coupled to a cooling device.

14. The rheometer of claim 13, wherein said support part is supported on said cooling device at a side of said support part facing away from the sample.

15. The rheometer of claim 13, wherein said cooling device has an opening through which the sample can be observed via a camera.

* * * * *